United States Patent
Hansen

(10) Patent No.: US 9,125,762 B2
(45) Date of Patent: Sep. 8, 2015

(54) PROSTHESIS COMPRESSING ARRANGEMENT

(71) Applicant: COOK MEDICAL TECHNOLOGIES LLC, Bloomington, IN (US)

(72) Inventor: Palle Munk Hansen, Bjaeverskov (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 249 days.

(21) Appl. No.: 13/785,596

(22) Filed: Mar. 5, 2013

(65) Prior Publication Data

US 2013/0245744 A1    Sep. 19, 2013

(30) Foreign Application Priority Data

Mar. 14, 2012 (GB) .................................. 1204506.8

(51) Int. Cl.
*A61F 2/95* (2013.01)
*A61F 2/966* (2013.01)

(52) U.S. Cl.
CPC . *A61F 2/95* (2013.01); *A61F 2/966* (2013.01); *A61F 2002/9522* (2013.01); *Y10T 29/49909* (2015.01); *Y10T 29/49913* (2015.01); *Y10T 29/49925* (2015.01); *Y10T 29/53917* (2015.01)

(58) Field of Classification Search
CPC ... A61F 2/95; A61F 2002/9522; A61F 2/966; Y10T 29/49913; Y10T 29/49909; Y10T 29/49925; Y10T 29/53917
See application file for complete search history.

(56) References Cited

U.S. PATENT DOCUMENTS

| 6,074,381 | A | 6/2000 | Dinh et al. |
| 6,240,615 | B1 | 6/2001 | Kimes et al. |
| 2005/0234537 | A1 | 10/2005 | Edin |
| 2009/0259287 | A1 | 10/2009 | Valaie |
| 2010/0043197 | A1 | 2/2010 | Abbate et al. |

FOREIGN PATENT DOCUMENTS

| EP | 0826346 A1 | 3/1998 |
| EP | 1836998 A1 | 9/2007 |
| WO | WO 01/21110 A1 | 3/2001 |

OTHER PUBLICATIONS

Search Report for Great Britain Patent Application U.S. Appl. No. 1204506.8 dated Mar. 27, 2012, 1 page.
Combined Search and Examination Report under Sections 17 & 18(3) for Great Britain Patent Application Serial No. 1204506.8 dated Mar. 28, 2012, 1 page.
Examination Report for Great Britain Patent Application Serial No. 1204506.8 dated Jan. 7, 2014, 2 pages.
The Extended Search Report for European Patent Application Serial No. 13 275 060.5 dated Jul. 3, 2013, 8 pages.
Examination Report for European Patent Application Serial No. 13 275 060.5 dated May 7, 2015, 5 pages.

*Primary Examiner* — John C Hong
(74) *Attorney, Agent, or Firm* — Brinks Gilson & Lione

(57) ABSTRACT

A prosthesis is compressed in a device by being wrapped in a flexible sheet inside a cartridge, the opposite edges of the sheet being led out through a longitudinal slit in the cartridge and attached respectively to the outer surface of the cartridge and the inner surface of a surrounding shell; subsequent relative rotation of the shell pulls the sheet outwardly of the cartridge causing compression of the prosthesis. Stop projections are provided to limit the rotation to less than one complete revolution. End pieces of the device have tubes aligned with the prosthesis when compressed, and a pusher rod is pushed through the tubes to push the prosthesis into an introducer sheath. The or each end piece may incorporate a ratchet mechanism to prevent rotation in the wrong direction.

20 Claims, 2 Drawing Sheets

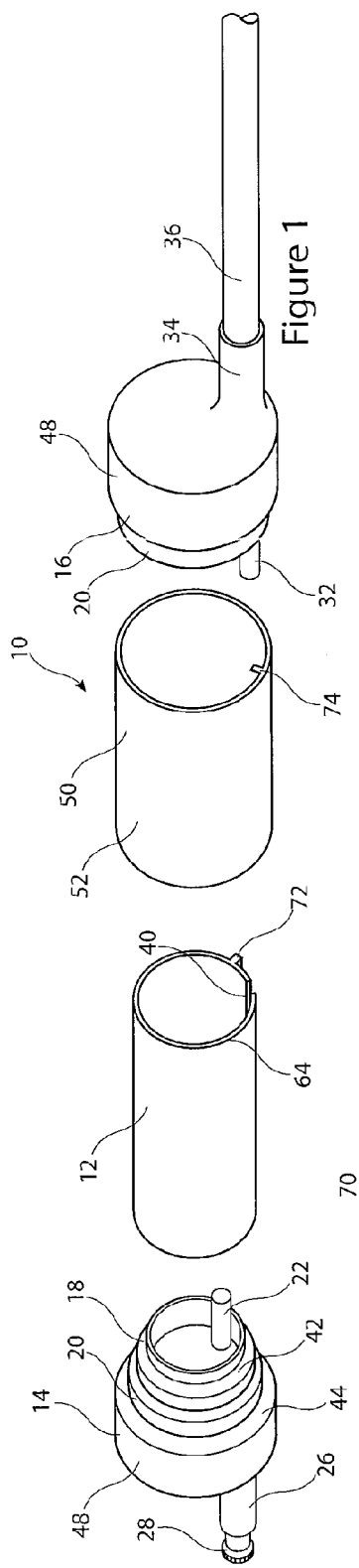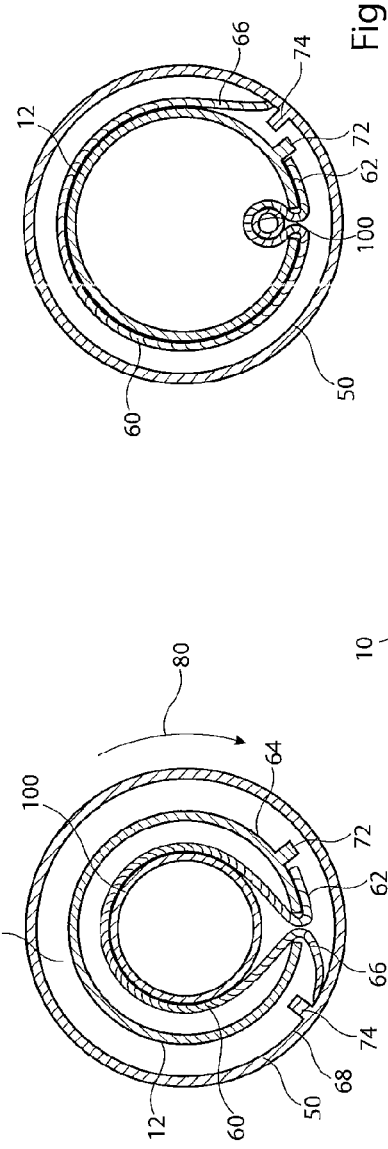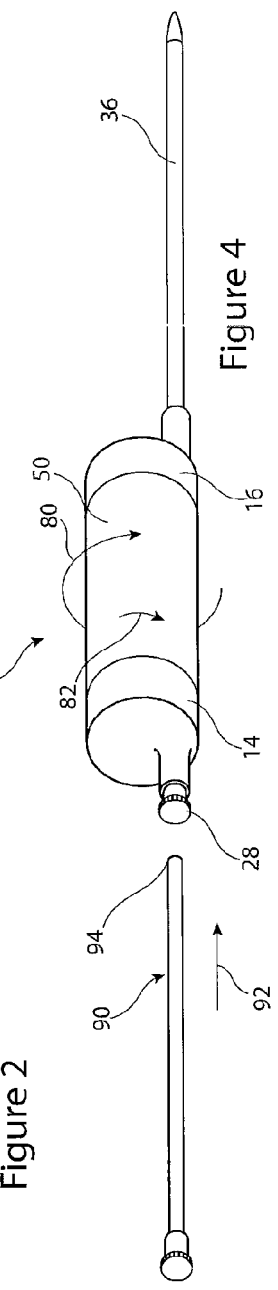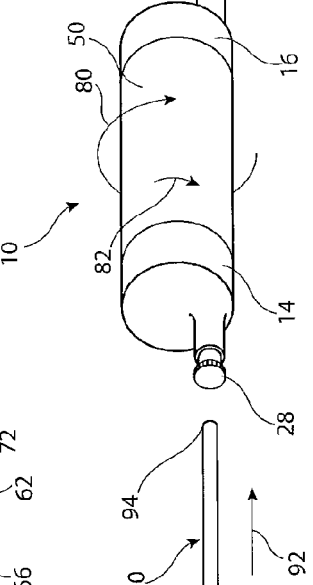

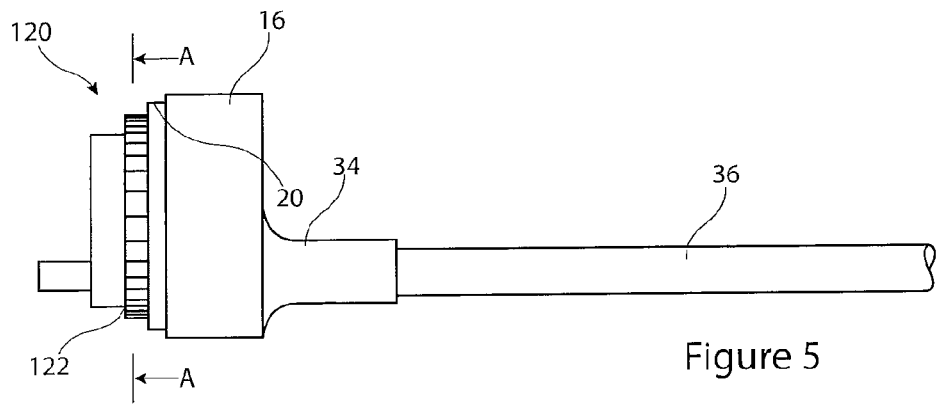
Figure 5
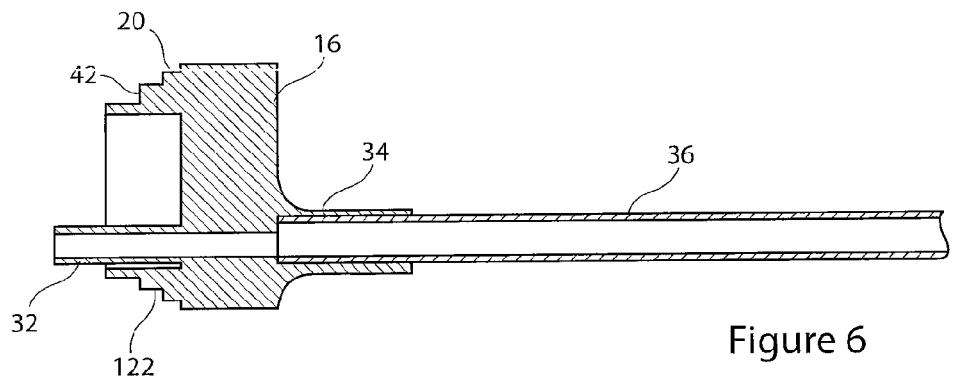
Figure 6
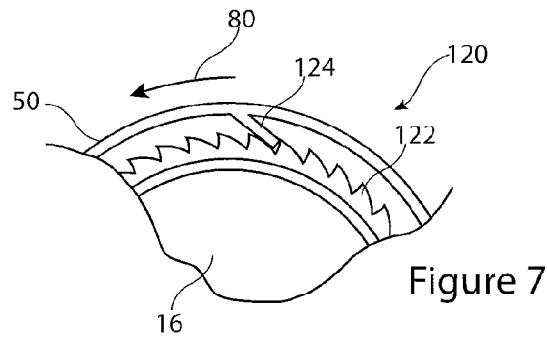
Figure 7
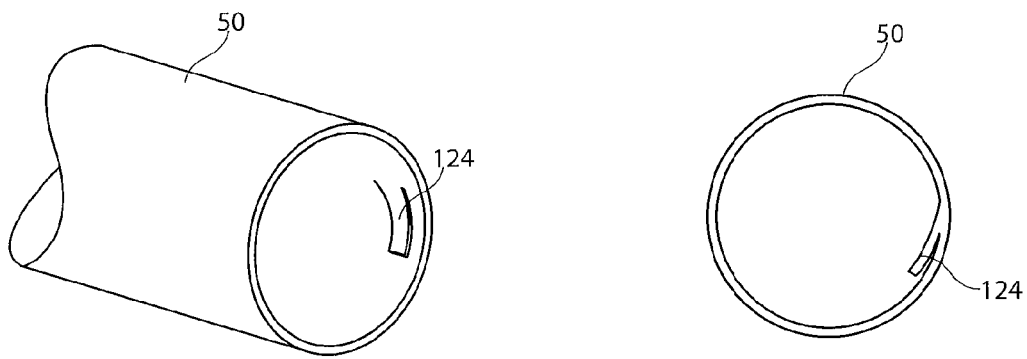
Figure 8
Figure 9

PROSTHESIS COMPRESSING ARRANGEMENT

This application claims the benefit of the filing date of United Kingdom (GB) patent application number 1204506.8, filed Mar. 14, 2012, which is hereby incorporated by reference herein.

The present invention relates to a prosthesis compressing arrangement and more particularly to a device and method for crimping a stent member before insertion into an introducer device.

Stent members and other prosthetic and intraluminal medical devices, after deployment into the lumen of a body vessel of patient, occupy substantially the whole cross-section of the lumen. Because the system for introducing the stent member into a desired deployment location has to navigate narrow passageways of the patient's vasculature, the stent member has to be compressed or crimped before introduction into the body.

For many stent members, the need to compress them presents no problem, because this can be conveniently undertaken at the manufacturing stage. However, some types of prosthetic devices are unsuitable for handling in this way. As recognised in US 2009/0259287, some tissue-based devices need to be maintained in appropriate fluid during storage and thus keeping them in a compressed configuration is preferably avoided. Aspects of the present invention are based on the recognition that long-term storage in a compressed condition could also be disadvantageous for certain biodegradable polymers and other materials, where the risk of permanent setting is a possibility. It would be a serious risk to a patient, if an inserted prosthesis did not fully and substantially immediately expand to its deployed size when required.

US2009/0259287 discloses a device and method for compressing and loading a prosthesis just before treatment of a patient. A medical prosthesis is placed upon a flat body and then compressed by wrapping the body around the prosthesis. The prosthesis is then moved out by a pushing force into a suitable delivery device.

Aspects of the present invention seek to provide an improved device and method. In particular, aspects of the invention seek to provide a device and method which are simple and convenient to use. Aspects of the invention also seek to provide a device and method which maintain the prosthesis in a sterile environment.

According to a first aspect of the present invention there is provided a device for compressing a prosthesis comprising a generally cylindrical housing having a longitudinal axis, and comprising first and second parts which are rotatable relative to each other about said axis, and at least one flexible member arranged within the housing and defining a space for accommodating an expanded prosthesis, respective parts of the flexible member being attached to the first and second relatively rotatable parts such that, upon relative rotation thereof, the size of the space is reduced so as to be capable of compressing the prosthesis.

Preferably the flexible member comprises a substantially rectangular sheet. This permits an even compression of an accommodated prosthesis. In preferred arrangements the sheet has first and second longitudinal edges which are substantially parallel to said axis, the first longitudinal edge being attached to the first rotatable part and the second longitudinal edge being attracted to the second rotatable part. Preferably the first rotatable part surrounds the second rotatable part, and the second rotatable part has a longitudinal slit therethrough, the flexible member part being arranged within the said second rotatable part, wherein the first longitudinal edge passes through said slit and is attached to the inner surface of the first rotatable part, and wherein the second longitudinal edge passes through said slit and is attached to the outer surface of the second rotatable part adjacent to the said slit.

In a preferred embodiment, adjacent to the first longitudinal edge, there is provided a projection on the inner surface of the first rotatable part, and adjacent to the second longitudinal edge, there is provided a projection on the outer surface of the second rotatable part, the disposition of the projections being such as to prevent relative rotation of the rotatable parts of more than one revolution. This ensures that an accommodated prosthesis is compressed to a controlled extent. If the prosthesis is not compressed enough, it will not fit into its introducer system. If the prosthesis is compressed too much, it may not be possible to remove it from the compression device and, in particular, to release it from the flexible member; furthermore damage could be caused to the prosthesis.

The device can further comprise a detent mechanism for retaining the rotatable parts in a rotated configuration.

Preferably, the device comprises first and second end pieces, said first part being rotatably mounted on said end pieces and said second part being non-rotatably mounted on said end pieces. At least one of the end pieces may have a ratchet mechanism for retaining the rotatable parts in a rotated configuration. This serves to retain the prosthesis in its compressed configuration when rotation has been completed. It also serves to prevent reverse rotation should the compression procedure be interrupted at any point.

Each end piece may have an outer generally cylindrical wall, an intermediate cylindrical wall, the outer surface of which is arranged to be rotatably connected to said first part, and an inner cylindrical wall, the outer surface of which is arranged to be non-rotatably connected to said second part. A tube may be provided adjacent to the inner surface of the inner cylindrical wall of each end piece, said tube extending longitudinally completely through the respective end piece, and the tubes in the end pieces being mutually aligned. This provides a convenient arrangement for dispensing the prosthesis from the device after compression.

The invention also provides a combination of the above device with a pusher rod, said pusher rod being sized to pass through the tube of one of the end pieces, through said second rotatable part, and into the tube of the other of the end pieces.

A mechanism may be provided for delivering a tactile, acoustic and/or visual signal when one complete revolution is approached. This conveniently indicates to a user that the compression procedure has been satisfactorily completed. It also warns the user against further rotation, which might produce damage.

According to a second aspect of the present invention there is provided a method of compressing a prosthesis comprising providing a housing having first and second generally cylindrical parts which are relatively rotatable, with the first housing part being arranged to surround the second housing part, the second housing part having a longitudinal slit, and providing a flexible enclosure member having first and second opposite ends, placing the enclosure member inside the second housing part, passing the first end of the enclosure member through said slit and attaching it to an adjacent part of the inner surface of the first housing part, passing the second end of the enclosure member through said slit and attaching it to an adjacent part of the outer surface of the second housing part, placing an expandable prosthesis in its expanded configuration within the enclosure member, and relatively rotating the first and second housing parts whereby to tighten the enclosure member around the prosthesis to compress it.

According to a third aspect of the present invention there is provided a method of installing an expandable prosthesis in an introducer apparatus comprising in a first stage, placing an expanded prosthesis in a generally cylindrical housing having a longitudinal axis and comprising first and second parts which are rotatable relative to each other about said axis, the housing accommodating at least one flexible member which defines an interior space in which the expanded prosthesis is placed, respective parts of the flexible member being attached to the first and second relatively rotatable parts, and, in a second stage, relatively rotating the first and second parts to cause the size of the space to be reduced so as to compress the prosthesis, connecting an end of the housing to the introducer apparatus, and subsequently urging the prosthesis longitudinally from the end of the housing into the introducer apparatus.

A preferred embodiment of the present invention will now be described, by way of example only, with reference to the accompanying drawings, of which:

FIG. 1 shows an exploded view of a prosthesis compressing and loading device in accordance with the present invention;

FIG. 2. is a cross-section of the device of FIG. 1 accommodating a prosthesis in an expanded condition;

FIG. 3 is a view corresponding to FIG. 2 with the prosthesis in a compressed condition;

FIG. 4 is a perspective view of the device of FIG. 1 in use;

FIG. 5 is an enlarged side view of part of the device of FIGS. 1 to 4;

FIG. 6. is a sectional side view corresponding to FIG. 5;

FIG. 7. is a partial further enlarged cross-sectional view of the device along the line A-A in FIG. 5; and FIGS. 8 and 9 are perspective and end views of a component of the device.

Referring now to the drawings, FIG. 1 shows a prosthesis compressing and loading device 10 in accordance with first embodiment of the present invention. The device comprises a housing part in the form of a stent cartridge 12, which is located between proximal and distal end pieces 14, 16. The cartridge 12 is fixedly i.e. non-rotatably mounted on and between inner cylindrical walls constituted by tubular stubs or projections 18 of the respective end pieces.

Located adjoining the inner surface of the tubular projection 18 of the end piece 14 and fixed thereto is a tube 22 of much smaller diameter. Tube 22 projects axially beyond the wall of the tubular projection 18. In the opposite axial direction, tube 22 extends completely through the end piece 14 and terminates in a mouth 26. In the configuration of FIG. 1, mouth 26 is closed by a removable cap or plug 28.

End piece 16 is substantially a mirror image of end piece 14. Accordingly, a tube 32 similar to tube 22 extends axially towards end piece 14 from a tubular projection (not shown) of end piece 16, and projects therefrom. Tube 32 extends completely though the end piece 16 and terminates in a mouth 34. Mouth 34 is slightly wider than the tube 32 as shown in FIG. 6. The mouth accommodates the end of an introducer sheath 36 and is in communication with the interior thereof.

The tubular projection 18 on end piece 14 and the corresponding tubular projection of end piece 16, terminates at a first annular wall 42. An intermediate cylindrical wall 20 extends between the radially outer edge of wall 42 and the radially inner edge of a second cannula wall 44. The radially outer edge of wall 44 meets an outer cylindrical wall 48 of the respective end piece.

Cartridge 12 is in the form of a spilt cylinder and has a longitudinal slit 40 along its entire length. It is surrounded by a further housing part in the form of a cylindrical outer shell 50, with a circumferential gap of 70, FIG. 2, being formed therebetween. Shell 50 is rotatably mounted at its ends on the intermediate cylindrical walls 20 of the end pieces 14, 16. When the device 10 is assembled, the outer surface 52 of shell 50 is flush with the cylindrical walls 48 of the end pieces (see FIG. 4).

The device accommodates a prosthesis in the form of a stent member 100, in particular a stent graft member containing one or more biodegradable materials, such as biodegradable polymers, or bioabsorbable materials. With such materials, there is a risk of permanent setting if they are constrained for too long in a compressed condition. Examples of polymers which are particularly suitable are: poly-L, D-lactide, poly-L-lactide, poly-D-lactide, bioglass, poly(alpha hydroxy acid), polyglycolic acid, polylactic acid, polycaprolactone, polydioxanone, polyglucanate, polylactic acid-polyelethelene oxide copolymers, tyrosine derived polycarbonate, polyglycolide, modified cellulose, collagen, poly(hydroxybutyrate), polyanhydride, polyphosphoester, poly(amino acids) or combinations thereof. Other examples of suitable bioabsorbable materials for the stent member are alloys in which the main component is magnesium, tungsten or iron.

To load the cartridge 12 with the prosthesis 100, the prosthesis in its expanded configuration is encircled by a rectangular sheet of plastic material 60, see FIG. 2. The length of the stent member 100 and the surrounding sheet 60 corresponds to the distance between the ends of tubes 22 and 32 when the device 10 is assembled, or slightly less.

A strip of the sheet material along one longitudinal edge 62 thereof is fixedly attached to the outer surface 64 if the cartridge 12 along one side of the longitudinal slit 40. The opposite longitudinal edge 66 of the sheet 60 is fixedly attached to the inner surface 68 of the shell 50 as shown in FIG. 2.

Adjacent to the attached edge 62, a projection 72 extends along the outer surface 64 of cartridge 12. The height of the projection is substantially equal to three quarters of the width of the circumferential gap 70. A similar projection 74 extends along the inner surface 68 of shell 50 adjacent to the attached edge 66. The height of projection 74 is also substantially equal to three quarters of the width of the gap 70.

Manufacture of the device 10 is completed when the stent member 100 and sheet 60 have been installed as shown in FIG. 2, the edges 62, 64 of sheet 60 have been attached to the cartridge 12 and shell 50 respectively, and the cartridge 12 and shell 50 have been connected to the end pieces 14 and 16. The completely assembled device 10 is shown at the right of FIG. 4. The device is then placed in sterilized packaging for subsequent transport and storage.

When it is desired to deploy the device 10 in a patient, it is removed from its packaging. A user then rotates shell 50 in the direction indicated by arrows 80, FIGS. 3 and 4, relative to the end pieces 14, 16 and to cartridge 12. The correct direction of rotation is indicated by one or more appropriate markings 82 on outer surface 52. The rotation has the effect of moving the longitudinal edge 66 of sheet 60 clockwise around the exterior of cartridge 12. As more of sheet 60 passes through slit 40, the portion of the sheet remaining inside cartridge 12 compresses or crimps the stent member 100.

The compression process terminates when the shell 50 has completed almost one revolution. At this time, the projection 74 engages projection 72 to prevent further rotation. The engagement of the projection produces a sound which gives an indication to a user to stop turning. The stent member 100 is now in its fully compressed configuration, FIG. 3, inside the short portion of sheet material remaining within cartridge 12.

In the next stage of the deployment procedure, the stent member 100 is moved into introducer sheath 36. Cap 28 is first removed from a mouth 26 and a pusher rod 90 is inserted into tube 22. Axial movement by the user of the pusher rod in the direction of arrow 92, causes the end 94 of the rod to engage the proximal end of the stent member 100 and to push the entire stent member into the introducer sheath 36. The length of the pusher rod is equal to or slightly greater than the length of the device 10.

Once the stent member 100 is completely inside the sheath 36, the sheath 36 is disconnected from the mouth 34 and installed in an introducer system for a subsequent surgical procedure.

The above-described arrangement has numerous advantages. In particular, it provides a simple procedure for compressing a prosthesis which is error-free and intuitive. The correct way to operate the device is indicated by marking 82, and the correct time to cease rotation is indicated by touch and acoustically, when projections 72 and 74 engage. Accordingly, the compression of the stent member 100 does not need to be restricted geographically to the factory but can be undertaken on site by a user requiring little extra training. Moreover, the compression procedure can occur within a sterile environment.

Instead of, or in addition to, stent members incorporating bioabsorbable/biodegradable materials, the prosthesis 100 can be one which needs to be maintained in an appropriate fluid during pre-operative storage.

The provision of the stop projections 72, 74 has the advantage of limiting compression of the prosthesis to the predetermined amount. If the prosthesis were compressed too tightly within sheet 60, it would not be possible to overcome the frictional forces to push the prosthesis into the introducer sheath. In the described embodiment, the surface of the sheet 60 is sufficiently smooth to permit the necessary relative sliding movement for the prosthesis to satisfactorily enter the introducer sheath.

The heights of the stop projections 72, 74 are such that they reliably engage with each other in their FIG. 3 configuration to prevent further rotation. On the other hand, there is sufficient clearance between the top of the projection 72 and the inner surface 69 of the shell 50, and between the top of the projection 74 and the outer surface 64 of cartridge 12, that the projections do not interfere with the relative rotation of shell 50 to cartridge 12 as the stent member 100 is compressed.

Only a small portion of sheet 60 remains within the cartridge 12 surrounding the prosthesis at the end of the compression procedure as shown in FIG. 3. Accordingly, the device 10 achieves a substantial compression of the prosthesis. The cross-sectional area of the prosthesis can be compressed by a factor of 25 or more.

Each of the components of the device 10, i.e. cartridge 12 including strip 72, shell 50 including strip 74, end piece 14, end piece 16, cap 28 and sheath 36, is preferably made of molded plastic material such as nylon or ABS material. If desired, tubes 22, 32 may be made separately from the respective end pieces.

The longitudinal edges 62, 66 of the sheet 50 are preferably secured to cartridge 12 and shell 50 respectively by means of adhesive. Other suitable methods of attachment can be deployed such as a thermal bonding, riveting, stapling etc. Instead of a plastics sheet 60, a metallic foil or a textile material can be deployed. If desired, sheet 60 can be shorter than or larger than stent member 100; however, it is preferable that sheet 60 is at least as long as stent member 100 to ensure an even compression of the stent member.

The stop projections 72, 74, may extend across substantially all of circumferential gap 70 if desired. In this case, they assist in keeping cartridge 12 and shell 50 at a constant separation during relative rotation.

The stop projections 72, 74 can extend only along one or more portions of the length of the cartridge 12 and shell 50. They can have interconnecting formations which engage in the disposition shown in FIG. 3. The act of interconnection can produce the above-mentioned acoustic effect. In addition, the interconnection serves to hold the components of the device in their disposition shown in FIG. 3, so that there is no danger of relative rotation of the shell 50 in an anti-clockwise direction. This prevents re-expansion of the stent member 100 while the pusher rod 90 is being deployed. The projections 72, 74 can be omitted if desired.

In an alternative arrangement, another detent mechanism can be provided between cartridge 12 and shell 50 to hold them in a non-rotatable configuration once they have reached their relative disposition shown in FIG. 3.

In a further alternative arrangement, end piece 16 incorporates a detent device in the form of a ratchet mechanism 120, FIGS. 5 to 9. Ratchet teeth 122 are provided around the circumference of cylindrical wall 20 and formed integrally therewith. As shown in FIGS. 5 and 6, the ratchet teeth extend across substantially half of the width of wall 20 adjacent to the annular wall 42 of end piece 16. In addition, the outer diameter of the teeth 122 is slightly less than the diameter of the remainder of cylindrical wall 20.

At its end, the interior of the shell 50 has a resilient tongue portion 124. Tongue 124 is arranged to permit relative rotation of the shell 50 in the direction of arrow 80 by sliding over the teeth. Upon an attempt to rotate the shell 50 in the opposite direction, the tongue engages the steep side of one of the teeth which prevents such rotation.

The above-described arrangement assists in further reducing the risk of incorrect operation of the device 10 and prevents the stent member from re-expanding should the compression process to interrupted. Repeated compression and expansion of the stent member could allow it to become misshapen or even damaged.

The small step between wall 20 and teeth 122 ensures that the shell 50 can rotate freely on wall 20 without the teeth interfering with this.

The ratchet mechanism can incorporate a device for producing a different sound once the disposition of FIG. 3 has been reached. The ratchet mechanism can incorporate a limit device.

In a further modification, both end pieces 14, 16 incorporate a ratchet mechanism. In this case, the end pieces 14, 16 do not need to be mirror symmetrical. However, they are preferably mirror-symmetrical and, for ease of manufacture, further preferably identical.

Although shown in FIG. 1 as a part of device 10, the introducer sheath 36 may be connected at any suitable stage of the procedure. For example, it can be connected to device 10 after the compression procedure indicted in FIG. 4 has been completed. Until this point in the procedure, the mouth 34 can be covered with a cap or plug (not shown) similar to cap 28 to maintain a sterilized condition.

To maintain a high degree of sterilization, the entire compression and loading procedure can be carried out inside a transparent bag. In this case, the cartridge 12 and shell 50 do not need to be closed cylinders and thus can have open frameworks. Alternatively, cartridge 12 and shell 50 can be transparent to enable observation of compression of the prosthesis.

The prosthesis to be compressed can be a stent, a stent graft, a filter, a prosthetic heart valve, a venous valve, or other endoluminal device.

Instead of, or in addition to, tactile and acoustic indications, the device 10 may also provide a visual signal once the configuration of FIG. 3 has been reached.

Although a rectangular sheet 60 leads to an optimal even compression process, it can be replaced by a helical band, or even a helical wire, extending around the stent member. Relative rotation of the shell 50 still produces satisfactory compression of the stent member. A plurality of bands or wires may be provided between the cartridge 23 and the shell 50. Alternatively, a plurality of vanes or an iris mechanism can be used to compress or crimp the prosthesis.

If a prosthesis 10 is used which requires substantially less than one revolution of the shell 50 to compress it, one or both of the projections 72, 73 may be circumferentially shifted to permit only the required amounts of relative rotation.

The invention claimed is:

1. A device for compressing a prosthesis comprising a generally cylindrical housing having a longitudinal axis and coupling first and second parts which are rotatable relative to each other about said axis, and at least one flexible member arranged within the rotatable parts and defining a space for accommodating an expanded prosthesis, respective parts of the expanded member being attached to the first and second relatively rotatable parts such that, upon relative rotation thereof, the size of the space is reduced so as to be capable of compressing the prosthesis.

2. A device according to claim 1, wherein the flexible member comprises a substantially rectangular sheet.

3. A device according to claim 2, wherein the sheet has first and second longitudinal edges which are substantially parallel to said axis, the first longitudinal edge being attached to the first rotatable part and the second longitudinal edge being attached to the second rotatable part.

4. A device according to claim 3, wherein the first rotatable part surrounds the second rotatable part, and the second rotatable part has a longitudinal slit therethrough, the flexible member part being arranged within said second rotatable part, wherein the first longitudinal edge passes through said slit and is attached to an inner surface of the first rotatable part, and wherein the second longitudinal edge passes through said slit and is attached to an outer surface of the second rotatable part adjacent to said slit.

5. A device according to claim 4, wherein, adjacent to the first longitudinal edge, there is provided a projection on the inner surface of the first rotatable part, and adjacent to the second longitudinal edge, there is provided a projection on the outer surface of the second rotatable part, the projections being positioned such as to prevent relative rotation of the rotatable parts of more than one revolution.

6. A device according to claim 1, comprising stop projections which restrict relative rotation of the rotatable parts to less than one complete revolution.

7. A device according to claim 6 comprising a detent mechanism for retaining the rotatable parts in a rotatable configuration.

8. A device according to claim 1 comprising first and second end pieces, said first part being rotatably mounted on said end pieces and said second part being non-rotatably mounted on said end pieces.

9. A device according to claim 8, wherein at least one of said end pieces has a detent mechanism for retaining the rotatable parts in a rotated configuration.

10. A device according to claim 8, where each end piece has an outer generally cylindrical wall, an intermediate cylindrical wall, the outer surface of which is arranged to be rotatably connected to said first part, and an inner cylindrical wall, the outer surface of which is arranged to be non-rotatably connected to said second part.

11. A device according to claim 10, wherein a tube is provided adjacent to the inner surface of the inner cylindrical wall of each end piece, said tube extending longitudinally completely through the respective end piece, and the tubes in the end pieces being mutually aligned.

12. A device according to claim 11, wherein at least one of the tubes is provided with a removable cap or plug.

13. A device according to claim 11, in combination with a pusher rod, said pusher rod being sized to pass through the tube of one of the end pieces, through said second rotatable part, and into the tube of the other of the end pieces.

14. A device according to claim 1, wherein the first and second rotatable parts are limited to a relative rotation of less than one complete revolution.

15. A device according to claim 14, wherein a mechanism is provided for delivering a tactile, acoustic and/or visual signal when one complete revolution is approached.

16. A method of compressing a prosthesis comprising providing a housing having first and second generally cylindrical parts which are relatively rotatable, with the first cylindrical part being arranged to surround the second cylindrical part, the second cylindrical part having a longitudinal slit, and providing a flexible enclosure member having first and second opposite ends, placing the enclosure member inside the second cylindrical part, passing the first end of the enclosure member through said slit and attaching it to an adjacent part of an inner surface of the first cylindrical part, passing the second end of the enclosure member through said slit and attaching it to an adjacent part of an outer surface of the second cylindrical part, placing an expandable prosthesis in its expanded configuration within the enclosure member, and relatively rotating the first and second cylindrical parts whereby to tighten the enclosure member around the prosthesis to compress it.

17. A method according to claim 16, wherein the first and second housing parts are rotated by less than a complete revolution.

18. A method according to claim 16, wherein completion of the relative rotation of the housing parts is accompanied by an acoustic, tactile and/or visual signal.

19. A method according to claim 16, wherein relative rotation of the housing parts is permitted in only one direction.

20. A method of installing an expandable prosthesis in an introducer sheath comprising in a first stage, placing an expended prosthesis in a generally cylindrical housing, the housing accommodating at least one flexible member which defines an interior space in which the expanded prosthesis is placed and, in a second stage, acting upon the housing to cause the size of the space to be reduced so as to compress the prosthesis, connecting an end of the housing to the introducer sheath, and subsequently urging the prosthesis longitudinally from the end of the housing into the introducer sheath.

* * * * *